US010564123B2

(12) United States Patent
Al Ahmad et al.

(10) Patent No.: US 10,564,123 B2
(45) Date of Patent: Feb. 18, 2020

(54) BIOREACTOR SYSTEM AND METHOD OF OPERATING SAME FOR CELLULAR COMPOSITION IDENTIFICATION AND QUANTIFICATION

(71) Applicant: UNITED ARAB EMIRATES UNIVERSITY, Al Ain (AE)

(72) Inventors: Mahmoud F. Y. Al Ahmad, Al Ain (AE); Hina Laghari, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 47 days.

(21) Appl. No.: 15/977,472

(22) Filed: May 11, 2018

(65) Prior Publication Data

US 2018/0259484 A1    Sep. 13, 2018

Related U.S. Application Data

(63) Continuation-in-part of application No. 15/676,266, filed on Aug. 14, 2017, now Pat. No. 10,436,772, and (Continued)

(51) Int. Cl.
*G01N 27/48* (2006.01)
*G01N 25/00* (2006.01)
(Continued)

(52) U.S. Cl.
CPC .......... *G01N 27/48* (2013.01); *B01L 3/50273* (2013.01); *G01N 25/00* (2013.01); *G01N 25/72* (2013.01); *B01L 2300/0627* (2013.01)

(58) Field of Classification Search
CPC ..................................................... G01N 27/48
(Continued)

(56) References Cited

U.S. PATENT DOCUMENTS 3,678,151 A    7/1972   Horonick et al.
4,058,446 A    11/1977  Zirino et al.
(Continued)

FOREIGN PATENT DOCUMENTS

CA    1259374    9/1989
CN    101625358 A   1/2010
(Continued)

OTHER PUBLICATIONS

Oer,K. Haematology White Blood Cell Count. Nov. 28, 2011. Retrieved from https://www.youtube.com/watch?v=q6rfJQVSals.
(Continued)

*Primary Examiner* — Christopher E Mahoney
(74) *Attorney, Agent, or Firm* — Perry + Currier Inc.

(57) ABSTRACT

A system and method for continuously monitoring as well as identifying and quantifying intracellular components in a cell culture such as microalgal culture of a bioreactor is described. This is done to determine an optimum concentration of intracellular components of interest, such as lipids. The method may be integrated directly with the cultivation chamber to conduct real-time measurements to quickly obtain accurate and continuous information that may be used as feedback to control the cultivation growth conditions. Such characterization may provide highly relevant data to determine if the culture is ready for biofuel processing. If the culture is not ready for biofuel processing, the data allows for the modification of the growth condition in the microalgae culture in order to achieve the desired concentration of the microalgal intracellular component of interest for biofuel processing.

20 Claims, 3 Drawing Sheets

Related U.S. Application Data a continuation-in-part of application No. 15/121,958, filed as application No. PCT/IB2014/064042 on Aug. 25, 2014, now Pat. No. 10,078,067, application No. 15/977,472, which is a continuation-in-part of application No. 15/121,647, filed as application No. PCT/IB2015/053861 on May 25, 2015, now Pat. No. 10,416,093.

(60) Provisional application No. 62/002,883, filed on May 25, 2014.

(51) Int. Cl.
 *B01L 3/00* (2006.01)
 *G01N 25/72* (2006.01)

(58) Field of Classification Search
 USPC ........................................................ 324/71.1
 See application file for complete search history.

(56) References Cited

U.S. PATENT DOCUMENTS

| | | | |
|---|---|---|---|
| 5,476,797 | A | 12/1995 | Matsunaga |
| 6,069,011 | A | 5/2000 | Riedel |
| 6,541,617 | B1 | 4/2003 | Bamdad et al. |
| 6,905,586 | B2 | 6/2005 | Lee et al. |
| 8,742,773 | B2 | 6/2014 | Elder et al. |
| 2004/0124084 | A1 | 7/2004 | Lee et al. |
| 2008/0050769 | A1 | 2/2008 | Huang et al. |
| 2010/0089774 | A1 | 4/2010 | Manohar et al. |
| 2012/0116687 | A1* | 5/2012 | Kanderian ............ C12Q 1/6827 702/20 |
| 2014/0024044 | A1 | 1/2014 | Choi et al. |
| 2014/0323350 | A1 | 10/2014 | Nguyen et al. |
| 2015/0122669 | A1 | 5/2015 | Davis et al. |
| 2016/0251703 | A1 | 9/2016 | Gilboa-Geffen et al. |
| 2017/0095611 | A1 | 4/2017 | Wang et al. |
| 2017/0173578 | A1 | 6/2017 | Crooks et al. |
| 2017/0350848 | A1 | 12/2017 | Wang et al. |
| 2018/0316024 | A1* | 11/2018 | Horiai .................... H01M 4/926 |

FOREIGN PATENT DOCUMENTS

| | | |
|---|---|---|
| CN | 101676727 A | 3/2010 |
| CN | 104251810 A | 12/2014 |
| EP | 1688742 A1 | 8/2006 |
| EP | 2908130 A1 | 8/2015 |
| JP | 2002071585 A | 3/2002 |
| JP | 2007271412 A | 10/2007 |
| RU | 2192646 C1 | 11/2002 |
| WO | WO-0210754 A2 | 2/2002 |
| WO | WO-2010006253 A1 | 1/2010 |
| WO | WO-2010099618 A1 | 9/2010 |
| WO | WO-2010126897 A1 | 11/2010 |
| WO | WO-2012102584 A2 | 8/2012 |
| WO | WO-2014076506 A1 | 5/2014 |

OTHER PUBLICATIONS

USPTO, Ex Parte Quayle Action, Mar. 4, 2019, re U.S. Appl. No. 15/676,266.
Azmir, Jannatul, et al. "Techniques for extraction of bioactive compounds from plant materials: a review" Journal of Food Engineering 117.4 (2013): 426-436.
Ben-Iwo, Juliet, Vasilije Manovic, and Philip Longhurst. "Biomass resources and biofuels potential for the production of transportation fuels in Nigeria." Renewable and Sustainable Energy Reviews 63 (2016): 172-192.
Bleakley, Stephen, and Maria Hayes. "Algal proteins: extraction, application, and challenges concerning production." Foods 6.5 (2017): 33.
Erickson, Brent, and Paul Winters. "Perspective on opportunities in industrial biotechnology in renewable chemicals." Biotechnology journal 7.2 (2012): 176-185.
Fakhry, Eman M., and Dahlia M. El Maghraby. "Lipid accumulation in response to nitrogen limitation and variation of temperature in Nannochloropsis saline." Botanical studies 56.1 (2015): 6.
Fu, Chun-Chong, et al. "Hydrolysis of microalgae cell walls for production of reducing sugar and lipid extraction." Bioresource Technology 101.22 (2012): 8750-8754.
Gonzalez Lopez, Cynthia Victoria, et al. "Protein measurements of microalgal and cyanobacterial biomass." Bioresource Technology 101.19 (2010): 7587-7591.
Govender, Trisha, et al. "BODIPY staining, an alternative to the Nile Red fluorescence method for the evaluation of intracellular lipids in microalgae." Bioresource technology 114 (2012): 507-511.
Grosso, Clara. et al. "Alternative and efficient extraction methods for marine-derived compounds." Marine Drugs 13.5 (2015): 3182-3230.
Juneja, Ankita, Ruben Ceballos, and Ganti Murthy. "Effects of environmental factors and nutrient availability on the biochemical composition of algae for biofuels production: a review." Energies 6.9 (2013): 4607-4638.
Written Opinion dated Jan. 14, 2015 for International Patent Application No. PCT/IB2014/064042. 7 pages.
Bligh, E. Graham, and W. Justin Dyer. "A rapid method of total lipid extraction and purification." Canadian journal of biochemistry and physiology 37.8 (1959): 911-917.
Breil, Cassandra, et al. ""Bligh and Dyer" and Folch Methods for Solid-Liquid-Liquid Extraction of Lipids from Microorganisms. Comprehension of Solvatation Mechanisms and towards Substitution with Alternative Solvents." International journal of molecular sciences 18.4 (2017): 708.
Cadenas, Alfredo, and Sara Cabezudo. "Biofuels as sustainable technologies: perspectives for less developed countries." Technological Forecasting and Social Change 58.1-2 (1998): 83-103.
Chen, Chun-Yen, et al. "Microalgae-based carbohydrates for biofuel production." Biochemical Engineering Journal 78 (2013): 1-10.
Chen, Yimin, and Seetharaman Vaidyanathan. "Simultaneous assay of pigments, carbohydrates, proteins and lipids in microalgae." Analytica chimica acta 776 (2013): 31-40.
Converti. Attilio, et al. "Effect of temperature and nitrogen concentration on the growth and lipid content of Nannochloropsis oculata and Chlorella vulgaris for biodiesel production." Chemical Engineering and Processing: Process Intensification 48.6 (2009): 1146-1151.
Pereira Da Costa, Marion, and Carlos Adam Conte-Junior. "Chromatographic methods for the determination of carbohydrates and organic acids in foods of animal origin." Comprehensive Reviews in Food Science and Food Safety 14.5 (2015): 586-600.
Dai, Shuxi, et al. "Structural properties and Raman spectroscopy of lipid Langmuir monolayers at the air-water interface." Colloids and surfaces B: Biointerfaces 42.1 (2005): 21-28.
Hannon, Michael, et al. "Biofuels from algae: challenges and potential." Biofuels 1:5 (2010): 763-784.
Jena, Jayashree, et al. "Microalgae of Odisha coast as a potential source for biodiesel production." World Environment 2.1 (2012): 11-16.
Kim, Garam, Ghulam Mujtaba. and Kisay Lee. "Effects of nitrogen sources on cell growth and biochemical composition of marine chlorophyte *Tetraselmis* sp. for lipid production." Algae 31.3 (2016): 257-266.
Krienitz, Lothar, and Manfred Wirth. "The high content of polyunsaturated fatty acids in Nannochloropsis limnetica (Eustigmatophyceae) and its implication for food web interactions, freshwater aquaculture and biotechnology." Limnologica-Ecology and Management of Inland Waters 36.3 (2006): 204-210.
Ranjith Kumar, Ramanathan, Polur Hanumantha Rao, and Muthu Arumugam. "Lipid extraction methods from microalgae: a comprehensive review." Frontiers in Energy Research 2 (2015): 61.
Layne, Ennis. "[73] Spectrophotometric and turbidimetric methods for measuring proteins." (1957): 447-454.

(56) References Cited

OTHER PUBLICATIONS

Liu, Zhi-Yuan, Guang-Ce Wang, and Bai-Cheng Zhou. "Effect of iron on growth and lipid accumulation in Chlorella vulgaris." Bioresource technology 99.11 (2008): 4717-4722.
Lohman, Egan J., et al. "An efficient and scalable extraction and quantification method for algal derived biofuel." Journal of microbiological methods 94.3 (2013): 235-244.
Ma, Xiao-Nian, et al. "Lipid production from Nannochloropsis." Marine drugs 14.4 (2016): 61.
Maehre, Hanne K., et al. "Protein Determination—Method Matters." Foods 7.1 (2018): 5.
Mata, Teresa M., Antonio A. Martins, and Nidia S. Caetano. "Microalgae for biodiesel production and other applications: a review." Renewable and sustainable energy reviews 14.1 (2010): 217-232.
Meriluoto, J. "Chromatography of microcystins." Analytica Chimica Acta 352. 1-3 (1997): 277-298.
Minhas, Amritpreet K., et al. "A review on the assessment of stress conditions for simultaneous production of microalgal lipids and carotenoids." Frontiers in microbiology 7 (2016): 546.
Oer, K., Course: Pharmacological Lab procedures: Haematology White Blood Cell Count, Nov. 28, 2011, Retrieved from the Internet: https://www.youtube.com/watch?v=q6rfJQVSals.
ISA/AU, International Search Report, dated Jan. 14, 2015, re PCT International Patent Application No. PCT/IB2014/064042.
ISA/AU, Written Opinion, dated Jan. 14, 2015, re PCT International Patent Application No. PCT/IB2014/064042.
ISA/AT, International Search Report, dated Aug. 13, 2015, re PCT International Patent Application No. PCT/IB2015/053861.
ISA/AT, Written Opinion, dated Aug. 13, 2015, re PCT International Patent Application No. PCT/IB2015/053861.
Rajvanshi, Shalini, and Mahendra Pal Sharma. "Micro algae: a potential source of biodiesel." Journal of Sustainable Bioenergy Systems 2.3 (2012): 49.
Ruangsomboon, Suneerat, Monthon Ganmanee, and Sakchai Choochote. "Effects of different nitrogen, phosphorus, and iron concentrations and salinity on lipid production in newly isolated strain of the tropical green microalga, Scenedesmus dimorphus KMITL." Journal of applied phycology 25.3 (2013): 867-874.
Curtis RE, Freedman DM. Ron E, Ries LAG, Hacker DG. Edwards BK, Tucker MA, Fraumeni JF Jr. (eds). New Malignancies Among Cancer Survivors: SEER Cancer Registries, 1973-2000. National Cancer Institute, NIH Publ. No. 05-5302. Bethesda, MD, 2006.
USPTO, Non-Final Rejection, dated Dec. 14, 2017, re U.S. Appl. No. 15/676,266.
EPO, Extended European Search Report, dated Feb. 28, 2018, re European Patent Application No. 14900596.9.
Leeds University. The Histology Guide: White blood cells. 2003. Retrieved from https://www.histology.leeds.ac.uk/blood/blood_wbc.php.
Higuera. Valencia. WBC (White Blood Cell) Count. Mar. 6, 2017. Healthline. Retrieved from: https://www.healthline.com/health/wbc-count.

Hanna, Darrin M., et al. "Detection of vesicular stomatitis virus using a capacitive immunosensor." 2005 IEEE Engineering in Medicine and Biology 27th Annual Conference. IEEE, 2006.
Arumugam, M., et al. "Influence of organic waste and inorganic nitrogen source on biomass productivity of Scenedesmus and Chlorococcum sp." Journal homepage: www. IJEE. IEEFoundation. org 2.6 (2011): 1125-1132.
Grigoryev, Y. "Cell Counting with aHemocytometer: Easy as 1, 2, 3". Dec. 12, 2014. BiteSizeBio. Retrieved from: https://bitesizebio.com/13687/cell-counting-with-a-hemocytometer-easy-as-1-2-3/.
Sakthivel, Ramasamy. "Microalgae lipid research, past, present: a critical review for biodiesel production, in the future." Journal of Experimental Sciences (2011).
Show, Pau, et al. "A holistic approach to managing microalgae for biofuel applications." International journal of molecular sciences 18.1 (2017): 215.
Simionato, Diana, et al. "Response of Nannochloropsis gaditana to nitrogen starvation includes a de novo biosynthesis of triacylglycerols, a decrease of chloroplast galactolipids and a reorganization of the photosynthetic apparatus." Eukaryotic cell (2013): EC-00363.
Tamburic, Bojan, et al. "The effect of diel temperature and light cycles on the growth of Nannochloropsis oculata in a photobioreactor matrix." PloS one 9.1 (2014): e86047.
Trzcinska, Magdalena, et al. "Genetic and morphological characteristics of two ecotypes of *Eustigmatos calaminaris* sp. nov. (Eustigmatophyceae) inhabiting Zn-and Pb-loaded calamine mine spoils." Fottea 14 (2014): 1-13.
Vrsanska, Martina, and Kumbar Vojtech. "A comparison of Biuret, Lowry and Bradford methods for measuring the egg's proteins." Mendel Net (2015): 394-398.
Wan, Chun, Feng-Wu Bai, and Xin-Qing Zhao. "Effects of nitrogen concentration and media replacement on cell growth and lipid production of oleaginous marine microalga Nannochloropsis oceanica DUT01." Biochemical engineering journal 78 (2013): 32-38.
Wells, Mark L., et al. "Algae as nutritional and functional food sources: revisiting our understanding." Journal of applied phycology 29.2 (2017): 949-982.
Wen, Zhiyou, and Michael Ben Johnson. "Microalgae as a feedstock for biofuel production." Virginia Tech Publication 442-886. (2009).
Yang, Xiaohan, et al. "Innovative biological solutions to challenges in sustainable biofuels production." Biofuel Production-Recent Developments and Prospects. InTech, 2011.
Yen, Hong-Wei, et al. "Microalgae-based biorefinery—from biofuels to natural products." Bioresource technology 135 (2013): 166-174.
Yu. Wei-Luen, et al. "Modifications of the metabolic pathways of lipid and triacylglycerol production in microalgae." Microbial cell factories 10.1 (2011): 91.
Zhang, Yun-Ming, et al. "Nitrogen starvation induced oxidative stress in an oil-producing green alga Chlorella sorokiniana C3." PloS one 8.7 (2013): e69225.
Zhu, Shunni, et al. "Characterization of lipid and fatty acids composition of Chlorella zofingiensis in response to nitrogen starvation." Journal of bioscience and bioengineering 120.2 (2015): 205-209.

\* cited by examiner

BIOREACTOR SYSTEM AND METHOD OF OPERATING SAME FOR CELLULAR COMPOSITION IDENTIFICATION AND QUANTIFICATION

CROSS-REFERENCE AND RELATED APPLICATION

This application is a continuation-in-part from U.S. application Ser. No. 15/676,266, which is a continuation-in-part from U.S. application Ser. No. 15/121,958, which is a national Stage of International Application No. PCT/IB2014/064042 filed on 25 Aug. 2014, the entirety of which are incorporated herein. This application is also a continuation-in-part from U.S. application Ser. No. 15/121,647, which is a national Stage of International Application No. PCT/IB2015/053861 filed on 25 May 2015, which claims the benefit of U.S. Provisional Application No. 62/002,883 filed on 25 May 2014, the entirety of which are incorporated herein.

TECHNICAL FIELD

This invention relates generally to a bioreactor system and method of operating same and more specifically, to a bioreactor system for in-situ cellular composition determination and quantification in cells, such as microalgae cells, and a method of operating same.

BACKGROUND

Biofuel, including biodiesel and other biohydrocarbons is considered to be a promising alternative to fossil fuels. Biofuel may be produced from different types of cells and cell components. For example, biofuel may be produced from microalgal lipids. To achieve commercially viable biodiesel production from microalgae, high biomass and high lipid content are required. However, the conditions favouring high biomass productivity usually result in low lipid accumulation, and vice versa. Under stress conditions, as growth rate drops, microalgae tend to accumulate larger lipid content. Thus, the requirements of high biomass and high lipid content are inherently contradictory and entail diligent optimization of process conditions. To achieve this, it is essential to be able to monitor lipid accumulation.

Microalgae are essentially microscopic algae typically found in freshwater and marine systems, mostly unicellular and can exist individually or in groups. According to the species, their sizes differ in range from a few micrometers to a few hundred micrometers. They are capable of performing photosynthesis and produce just about half of the atmospheric oxygen and simultaneously consume carbon dioxide. Microalgae are found at the base of the food web, which highlights their importance on earth, and provide energy for all the trophic levels above them.

Microalgae are attaining increasing attention due to their wide range of applications in biology and biotechnology industries. The demands of microalgae as biodiesel are on a leap in the modern era due to the increasing demand for fuels and environmental safety. The main features that make the biofuels a smart alternative to fossil fuels are that they are renewable sources of energy, environment friendly and are economically significant. They possess high biomass productivity, speedy lipid accumulation and can survive in saline water. Biofuels are expected to take the place of fossil fuels in the future due to the demand for clean energy, economic potential and renewable nature.

Microalgae are rich sources of carbohydrates, lipids and proteins which make them important sources of feedstock. The presence of long chain fatty acids, proteins and carbohydrates makes them important as components of health food supplements as well as various pharmaceutical industries.

Oleaginous microalgae like the *Chlorella, Nannochloropsis, Scenedesmus* species are particularly important sources of biofuels as well as feedstock due to the high levels of proteins and polyunsaturated fatty acids. The biomolecule components can be enhanced by manipulating the various parameters by subjecting them to stress, both genetic and environmental (light, temperature, nutrient depletion like carbon or nitrogen, light intensity, salinity or harvesting procedure).

High biomass growth rate coupled with high nutrient content can be achieved simultaneously in a bioreactor. Engineering the growth medium, proper selection of the algal strains, use of genetic engineering and use of suitable extraction methods can optimize nutrient content. The studies involving continuous monitoring of the food, biofuel and other coproduct production requires continuous monitoring of the biochemical components.

Proteins make up a large portion of the cellular membrane and are important components of a number of enzymes that carry out the various cellular activities. Some microalgal species like *Nannochloropsis* sp., *Dunaliela* sp. and *Chlorella* sp. are able to accumulate 25-60% of lipids/dry weight. Biochemical methods have been used for the extraction of proteins, carbohydrates and lipids. Such methods involved use of strong alkali, acid and organic solvents. The cells have strong cell walls and the alkali treatment used for protein extraction lyses the cell walls. The ethanol precipitation helps the carbohydrates to be extracted completely. Several methods tried for lipid extraction turned out to be not entirely satisfactory as there was loss or incomplete extraction of lipids and some of them were time consuming.

A vast majority of the conventional techniques that are used to determine the biomolecule components (carbohydrates, lipids, proteins, nucleic acids, vitamins etc.) of microalgae in a culture for a bioreactor are labor intensive and time consuming. These procedures make use of various methods and reagents that are disparaging and hazardous to health as well as the environment.

The accurate, continuous and rapid detection of the amounts of carbohydrates, lipids and proteins in microalgal cells in a culture container of a bioreactor are extremely crucial and highly demanded in the field while engineering the microalgae for the production of distinctive type of biofuels.

SUMMARY OF THE INVENTION

The current disclosure has several aspects. In one aspect of the invention, a method is described for characterizing intracellular components of a cell culture in a bioreactor system. An example of such cell cultures is microalgae cells. Other types of cells may be used. The method includes: providing a sample culture in at least one microfluidic channel of a microfluidic system of the bioreactor. The sample culture is extracted from the cell culture, which is contained in a cultivation chamber of the bioreactor. The method also includes the step of applying an alternating current to the at least one microfluidic channel, where the alternating current is configured to have a resistivity distinguishing frequency for a component of interest from the intracellular components. The method further includes obtaining a first thermal image of the sample culture before applying the alternating current to the at least one microfluidic channel and a second thermal image of the sample culture during applying the alternating current to the at least one microfluidic channel. Additionally, the method includes generating a heat profile of the sample culture from the first thermal image and the second thermal image, where the heat profile allows for distinguishing the component of interest from the rest of the intracellular components of the sample culture. The method also includes determining the amount of the component of interest in the sample culture based on the heat profile generated; and determining an amount of the component of interest in the cell culture based on the amount of the component of interest determined in the sample culture.

In some embodiments, the heat profile is generated by subtracting the first thermal image from the second thermal image of the sample culture.

In some embodiments, the resistivity distinguishing frequency for the component of interest is obtained by performing the initial steps of: providing a reference culture sample containing at least the component of interest, wherein the reference culture sample is deposited into the at least one microfluidic channel. The initial steps also include marking the component of interest in the reference culture sample by a marker, where the marker is configured to substantially not affect the resistivity of the component of interest, the rest of the intracellular components or any cultivation medium and to only identify the component of interest from the rest of the intracellular components and the cultivation medium in the reference culture sample. The initial steps further include applying alternating currents to the at least one microfluidic channel, where the alternating currents are configured to be sweeping over a frequency range. The initial steps further include measuring the resistivity of the marked component of interest for each frequency of the frequency range; and identifying the resistivity distinguishing frequency for the component of interest in the reference culture sample, where the resistivity of the marked component of interest represents the highest measured resistivity.

In some embodiments, the step of identifying the resistivity distinguishing frequency for the component of interest in the reference culture sample at the highest measured frequency is performed by: obtaining thermal images of the reference culture sample before and during applying the alternating currents; generating a heat profile of the reference culture sample based on the thermal images; and determining a heat signature of the marked component of interest based on the heat profile, where the heat signature corresponds to the highest identified temperature in the heat profile and corresponds to the resistivity of the marked component of interest when the alternating current with the resistivity distinguishing frequency is applied to the reference culture sample.

In a related embodiment, the method further comprises generating a reference library of the resistivity distinguishing frequency and the corresponding heat signature for each component of the intracellular components.

In a related embodiment, the step of characterizing the intracellular component of the sample culture comprises: selecting from the reference library the resistivity distinguishing frequency for the component of interest; and identifying if the component of interest is present in the sample culture based on comparing heat signature values from the generated heat profile for the sample culture with the heat signature value from the reference library.

In a related embodiment, where once the component of interest is identified, the step of characterizing the intracellular component of the sample culture further comprises determining the amount of the component of interest by determining, based on the heat signatures in the heat profile, a ratio of the identified component of interest to the intracellular components and the cultivation medium.

In some embodiments, the cell culture contains microalgae cells, the component of interest is lipids and the intracellular components are lipids, carbohydrates and proteins and the method is used for optimizing the lipids' content in the microalgae cells culture for biofuel processing.

In a related embodiment, the step of optimizing the lipids' content in the microalgae cells culture is performed by continuously monitoring in-situ the amount of lipids in samples extracted from the microalgae cells culture and determining that the microalgae cells culture is ready for biofuel processing when a pre-determined threshold of lipid content is achieved in the microalgae cell culture.

In a related embodiment, the method further comprises returning the samples extracted from the cell culture back to the cultivation chamber after characterizing the intracellular components in the samples.

In another aspect of the current disclosure, a system is described for characterizing intracellular components of a cell culture in a bioreactor. The cell culture may be microalgae cells or other types of cells. The system includes a cultivation chamber for housing the cell culture and a microfluidic system in fluid communication with the cultivation chamber. The microfluidic system having at least one microfluidic channel is configured for holding a sample culture which is extracted from the cell culture. The system also includes an electrical analyzer in electrical communication with the microfluidic system. The electrical analyzer is configured for applying to the at least one microfluidic channel an alternating current with a resistivity distinguishing frequency for a component of interest from the intracellular components. The system also includes a thermal camera configured for obtaining a first thermal image of the sample culture before exposing the at least one microfluidic channel to the alternating current and a second thermal image of the sample culture while exposing the at least one microfluidic channel to the alternating current. The system further includes a processor configured for generating a heat profile of the sample culture from the first thermal image and the second thermal image. The heat profile allows for distinguishing the component of interest from the rest of the intracellular components of the sample culture. The processor is also configured to identify and determine the component of interest in the sample culture and the cell culture based on the generate heat profile.

In another embodiment, the system further includes a micropump coupled to the microfluidic system and the cultivation chamber and is used for extracting the sample culture from the cultivation chamber and for depositing the extracted sample culture to the at least one microfluidic channel.

In some embodiments, the at least one microfluidic channel comprises more than one microfluidic channel. In a related embodiment, the more than one microfluidic channels are formed in the microfluidic system to be substantially parallel to one another and each of the more than one microfluidic channels is electrically coupled to the electrical analyzer. In related embodiments, the electrical analyzer is configured to supply either the same of different voltage and alternating current for each of the more than one microfluidic channels.

In another embodiment, the microfluidic system has an inlet in fluid communication with the cultivation chamber. The intel is configured for receiving the sample culture from the cultivation chamber and to allow the flow of cells of the sample culture in series such that the cells are positioned in the at least one microfluidic channel and are examined one at a time. In other embodiments, the cells may be positioned in the at least one microfluidic channel as a group and are examined as such.

In another embodiment, the microfluidic system has an outlet for discharging the sample culture after characterizing its intracellular contents. In a related embodiment, the outlet is in fluid communication with the cultivation chamber so that when the sample culture is discharged from the microfluidic system, the sample is returned to the cultivation chamber. In such embodiment, the bioreactor system is considered a closed system and the cell culture is preserved throughout the examination process of its intracellular content.

In another embodiment, the system further comprises sensors positioned near the at least one microfluidic channel. The sensors are configured for detecting the presence of the sample culture in the at least one microfluidic channel and for signaling the thermal camera about when to take images of the sample culture and when to deactivate. In other embodiment, in place of the sensors, the camera may be programmed on a timer for activation and deactivation and for taking thermal images of the sample culture.

In another embodiment, the system further comprising a memory storage device for storing a pre-determined a resistivity distinguishing frequency and corresponding heat signature corresponding to each component of the intracellular components. The memory storage device is accessible by the processor so that the processor is able to retrieve the resistivity distinguishing frequency for the component of interest and the heat signature of the component of interest to allow for the identification and quantification of the component of interest in the sample culture.

In any of the systems described above, the system is configured such that the cell culture is uniformly distributed and the nutritional conditioning is uniformly dispersed in the cultivation chamber.

Other aspects of the invention will be apparent as will be shown in the detailed description of the invention.

BRIEF DESCRIPTION OF THE DRAWINGS

The accompanying drawings illustrate non-limiting example embodiments of the present disclosure.

DETAILED DESCRIPTION

Throughout the following description specific details are set forth in order to provide a more thorough understanding to persons skilled in the art. However, well known elements may not have been shown or described in detail to avoid unnecessarily obscuring the disclosure. The following description of examples of the technology is not intended to be exhaustive or to limit the system to the precise forms of any example embodiment. Accordingly, the description and drawings are to be regarded in an illustrative, rather than a restrictive, sense.

The current disclosure relies on a concept of utilizing electrical conditioning of a cell subjected to an alternating electrical field in order to identify and quantify intracellular components of interest based on the reaction of the intracellular components to the electrical conditioning and the generation of heat by the cellular components as a bi-product of its reaction to the electrical conditioning. When the intracellular components of interest are lipids, the technique described in this disclosure allows for passively and non-invasively obtaining the lipids count in a cell culture accurately and without the need for labor intensive and time-consuming techniques. In this disclosure, the cell culture is sometime referred to as microalgae culture. However, it is to be understood that different cell types may be used and such cells may be unicellular or multicellular.

The use of electrical characteristics for the identification and quantification of biological analytes have been disclosed in U.S. patent application Ser. No. 15/121,958 which content is entirely incorporated herein by reference. Also, the use of electrical characteristics and selective staining agents for identification or white and red blood cells in a blood sample has been disclosed in U.S. patent application Ser. No. 15/676,266, which content is entirely incorporated herein by reference. The current disclosure focuses on a related technique for the identification and quantification of lipids and other cellular content in cell cultures which may be represented in an exemplary embodiment as unicellular organisms such as microalgae in a culture container of a bioreactor. However, it is to be understood that the same or similar techniques may be used for identification and quantification of other cells and biological or non-biological entities in a biological sample or cell culture.

Figure 1:
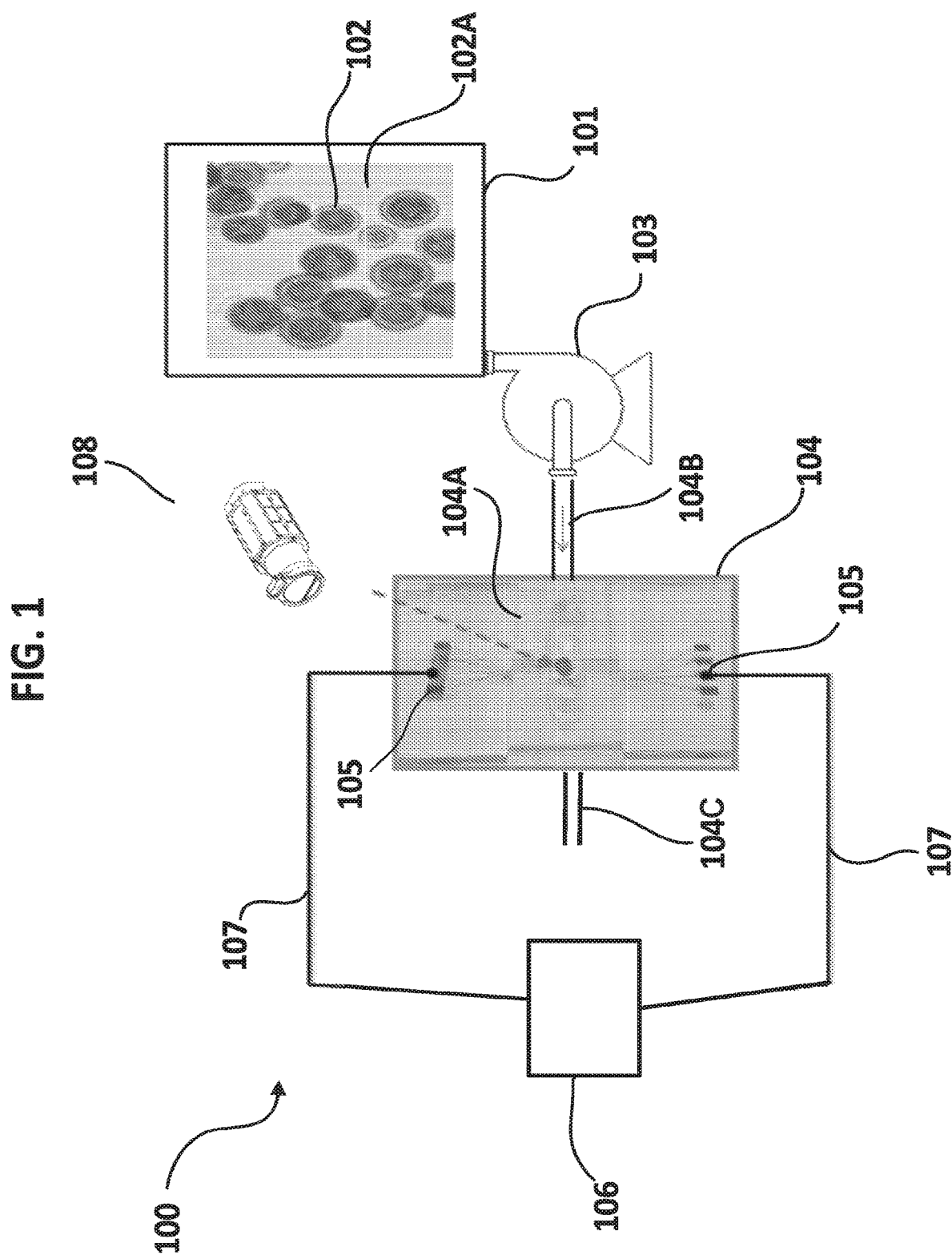
FIG. 1 shows a schematic view of a system for real time in-situ measurement of cell contents using thermal camera and electrical conditions according to an exemplary embodiment of the present disclosure.

Referring to FIG. 1, a schematic view of a bioreactor system 100 is described for in-situ identification and quantification of cellular components in living microalgal cells in accordance with an exemplary embodiment of the present invention. System 100 comprises a cultivation culture chamber 101, which contains a culture of microalgae living cells 102. The size of microalgae cells 102 may vary and may be in the range of 5 by 5 to 15 by 15 micrometers. System 100 also comprises a microfluidic system 104 composed of a series of microfluidic channels 104A. Microfluidic system 104 may be made from material known in the art for forming microfluidic systems. Microfluidic channels 104A may be itched or molded or may be formed in any other techniques known in the art. Microfluidic channels 104A may have different sizes. For example, the length and width of some microfluidic channels 104A may be such that the channels are allowed to fit a single microalgae cell. Other microfluidic channels may be sized to have a width and length capable of fitting a group of microalgae cells. Also, microfluidic channels 104A may be configured to have different patterns as will be described below. In the current embodiment, microfluidic system 104 is described to have an inlet 104B and an outlet 104C. The outlet may be used to discharge by-products like used cells 102 or medium 102A and other liquids out of the system.

System 100 is also shown to comprise a micropump 103 connected to the cultivation chamber 101 and is capable of extracting sample microalgae cells 102 from the cultivation chamber, allowing passage of the culture suspension containing cells 102 and the medium 102A at a pre-determined flow rate to microfluidic system 104 through inlet 104B. The flow rate as well as the operation of micropump 103 may be controlled by a control system (not shown), which may be internal or external to micropump 103. In some embodiments, the micropump may be optional and may be removed or replaced with similar devices for controlling and regulating fluidic flow.

Returning to the embodiment described in FIG. 1, inlet 104B may be sized to allow the flow of single microalgal cells 102 in series in the direction of flow. In other embodiments, Inlet 104B may be sized to allow the flow of multiple microalgal cells 102 in the direction of flow. The arrow shown inside inlet 104B in FIG. 1 represents the flow director of the suspension pumped by micropump 103 from culture chamber 101 to microfluidic system 104.

FIG. 1 also shows electrodes 105 connected to microfluidic channel 104A to allow for the generation of an electrical field across microfluidic channels 104A when a current is passed through electrodes 105. An electrical analyzer 106 is electrically connected to electrodes 105 via electrical connections 107 to establish and control a potential difference between the electrodes. The Electrical analyzer 106 is configured to provide voltage and alternating current to the electrodes 105 and to control the frequency of the alternating current supplied to electrodes 105 through electrical connections 107. In some embodiments, the electrical analyzer may be configured to provide a pulsating sweeping voltage and alternating current with a sweeping range of frequencies.

In the exemplary embodiment shown in FIG. 1, the electrical analyzer used is a Gamry™ Reference 600 electrical analyzer, which is a high performance, stand alone, computer-controlled potentiostat/galvanostat/ZRA that interfaces with a general computer via a USB. In some embodiments, the interface with the general processor may be done wirelessly. It is to be understood that other electrical analyzers known in the art may be used for the system described in the current disclosure. In the Example provided in FIG. 1, the computer is used for setting electrical conditions to apply electrical signals of pre-determined currents and frequencies to electrodes 105 of microfluidic system 104 through electrical connections 107. The settings of the AC electrical currents and frequencies may be controlled automatically by the system in accordance with system programming that may use values stored on a memory storage device, that may be enteral or external to the general processor. Additionally or in the alternative, the settings of the AC electrical currents and frequencies may be controlled manually by the user through a user interface.

In the embodiment shown in FIG. 1, the pattern of the microfluidic channels 104A is a simple design having a single microfluidic channel with an array of electrodes 105 on opposing side of the channel to allow for the generation of a distributed and uniform electrical field across the entire length of the microfluidic channel 104A when a voltage is applied by the electrical analyzer. In other embodiments, the microfluidic system may have different designs and patterns of microfluidic channels. For example, in some embodiments, system 104 may comprise a plurality of microfluidic channels of same or different sizes arranged substantially parallel to one another so that multiple distribution samples may be deposited into the microfluidic system for testing simultaneously and under same or different electrical conditions. In such embodiment, to allow for the testing of multiple distribution samples at the same time and subject to different electrical conditions, each of the channels may be configured to have its own array of electrodes along its opposing sides. In such embodiment, the electrodes may be connected to the same electrical analyzer or to multiple analyzer to provide the same or different electrical conditions across the different microfluidic channels.

The system described in FIG. 1 is used for identifying and quantifying cellular components of microalgal living cell in a bioreactor. This is done in-situ (on cite). So, no time is wasted in sending the sample microalgae to another location to have it tested for richness of lipids to determine if it is ready for use in biofuel processing. The identification of the cellular components of the microalgal cell is achieved by extracting a sample microalgal culture from the cultivation chamber to the microfluidic system using the micropump. Once in the microfluidic channels, the electrical analyser is used to subject the microalgal cells to a controlled AC current and frequency that generates an electrical field.

Different cellular components have different compositions. Due to their different composition, different cellular components will react differently under exposure to controlled electrical field caused by an AC electrical current with a pre-determined frequency. For example, different cellular components have different resistivity. Based on the intracellular composition of the cells, the distribution of the electrical current varies in the cell. The magnitude of the electrical current and frequency differs according to the interaction with the biomolecule (lipids and proteins) composition inside the cells. When a current/voltage of defined magnitude and frequency passes through the cell and encounters lipids or protein, resistance is generated. Also, heat is generated by such cellular components as a bi-product of their resistivity. In this current disclosure, the heat generated from such resistivity is measured and characterised in order to identify intracellular components of the microalgal cells and quantify them in-situ. In some embodiments, each cellular component may be isolated in a previous setting and its heat signature is characterised. Such information is later used to allow for identification of such components in a sample having a variety of cellular components based on analysis of the resulting heat profile of the entire cell.

Figure 2:
FIG. 2 shows a thermal image presenting a grey scale heat profile of lipids in a microalgal cell when exposed to an alternating current with a pre-determined frequency configured for optimizing the lipids resistivity in the microalgal cell.

FIG. 1 shows a thermal camera 108 positioned in the bioreactor system 100 and is used to capture the heat profile of cellular components of microalgal cells 102 deposited into the microfluidic channels 104A when subjected to an electrical field generated due to a supply by electrical analyser 106 of an AC electrical current to electrodes 105 through electrical connections 107. FIG. 2 shows a thermal image presenting a heat profile of intracellular components of a microalgal cell. In FIG. 2, proteins, lipids and carbohydrates are characterised using their individualized heat signatures subject to an application of a pre-determined alternating current, which will be described below. The heat or thermal profile presented in FIG. 2 is a grey scale characterisation of heat signatures for different intracellular components. In other embodiments, colour scale characterisation may be used.

Thermal camera 108 is connected to the microfluidic system 104 and may be used to capture the heat profile describing heat waves evoked by the cellular components of the microalgal cell 102 before and after the application of the electrical current. Different thermal cameras known in the art may be used. In the embodiment described in FIG. 1, thermal camera 108 is a high-resolution camera with a resolution capability and a temperature detection range sufficient to allow for capturing images of intracellular components and for profiling the heat signatures of such intracellular components.

In other embodiments, thermal camera 108 may be used in conjunction with a microscope for determining temperature profiles of samples on an intracellular level. In other embodiments, the camera may have multiple high-resolution lenses, that may be used to capture thermal images of different resolutions to accommodate different types and sizes of cells and/or cellular components of interest. The thermal camera may also be used to capture thermal images of more than one cell in the same image to allow for identification and quantification of intracellular components in a sample group of microalgal cells extracted from the cultivation chamber 101 in bioreactor 100.

The bioreactor may be configured according to any configuration known in the art to allow for the microalgal cells 102 contained in the cultivation chamber 101 to be uniformly dispersed in the medium and also to allow for nutritional conditioning to be uniformly distributed in the cultivation chamber. An aliquot or group sample extracted from a bioreactor cultivation chamber in accordance with such conditions may be considered as a good representation of the entire microalgal culture contained in the cultivation chamber. Therefore, identifying and quantifying the intracellular components of an aliquot or a group sample, would be a good estimation of the intracellular content of the entire microalgal culture contained in the cultivation chamber.

In some embodiments, thermal camera 108 may be configured to detect the presence of microalgal cells in the microfluidic channels using sensors or other known techniques in the art. Thermal camera 108 may also be programmed to work on a timer that may be synchronized with the pumping action of the micropump 103. In other embodiments, the activation, deactivation and operation of the thermal cameral, for example, may be linked to any one of change of weight of the microfluidic system due to a deposit of microalgal cells in the microfluidic channels and/or sensors located in or near the inlet and outlet of the microfluidic system. It is to be understood that the above are only exemplary and are not to limit the conditions for activation, deactivation and operation of the thermal cameral in the bioreactor system.

In some embodiments, the outlet of the microfluidic system may be used to reintroduce the sample microalgal cells extracted from the cultivation chamber back into the cultivation chamber. The feedback from the sample microalgal cells into the cultivation chamber may be achieved using micropumps or may be established by configuring the system to utilize gravity for such action. Alternatively, or in combination with the above, the feedback system may be configured to be a closed system and the action of returning the sample microalgal cells back to the cultivation chamber may be attributed to the pumping action of micropump 103.

Such feedback process allows for preserving the microalgal cells, which is possible due to the passive and non-invasive identification and detection technique utilised in the current disclosure. In such embodiments, the monitoring of the content of the cultivation chamber may be continuous. More specifically, the micropump may work continuously, or on programmed intervals, to extract aliquots from the medium of the cultivation chamber and pump such aliquots into the microfluidic system.

Alternating current is applied by the electrical analyser to the electrode arrays to generate an electrical field across the microfluidic channels. Thermal images of the microalgal cells in the microfluidic channels are obtained before and during the application of the electrical current. This may be achieved by programming the thermal camera to work on a timer. Once the thermal profiles are obtained, the microalgal cells are then returned to the cultivation chamber through the outlet of the microfluidic system.

The heat generated by the intracellular components of the microalgal cells in the system is the result of the resistivity of the intracellular components to the alternating current applied by the system. Varying the frequency in the AC electrical current is found to cause the intracellular components to behave differently from one another. For example, in a microalgal cell containing lipids, proteins and carbohydrates, subjecting the cell to an AC electrical current with a first frequency may cause the lipids to have a distinguished resistivity compared to that of the other intracellular components. Subjecting the same cell to an AC electrical current with a second frequency different from the first frequency may cause the proteins to have a distinguished resistivity compared to that of the other intracellular components.

The method of operating system 100 will now be described. The method allows for in-situ identifying and quantifying lipids and other intracellular components in a microalgae cell extracted from a cultivation chamber of bioreactor system 100. Microalgae cultures are usually subjected to growth conditions to condition them for biofuel processing. Under nitrogen deprivation, lipids are generated in the microalgae cell. Lipids are essential components for biofuel generation. So, a high concentration of lipids is necessary in a microalgae culture before sending such culture for biofuel processing. The method described allows for in-situ (on cite) examination of sample microalgae cells from the microalgae culture and the identification and quantification of the lipids inside the microalgae cells to determine if the culture is ready for biofuel processing. The results obtained allows for modification of the cultivation culture and/or the nutritional conditions to optimise lipid generation and achieve the desired concentration of lipids before sending the content of cultivation chamber for biofuel processing.

Figure 3:
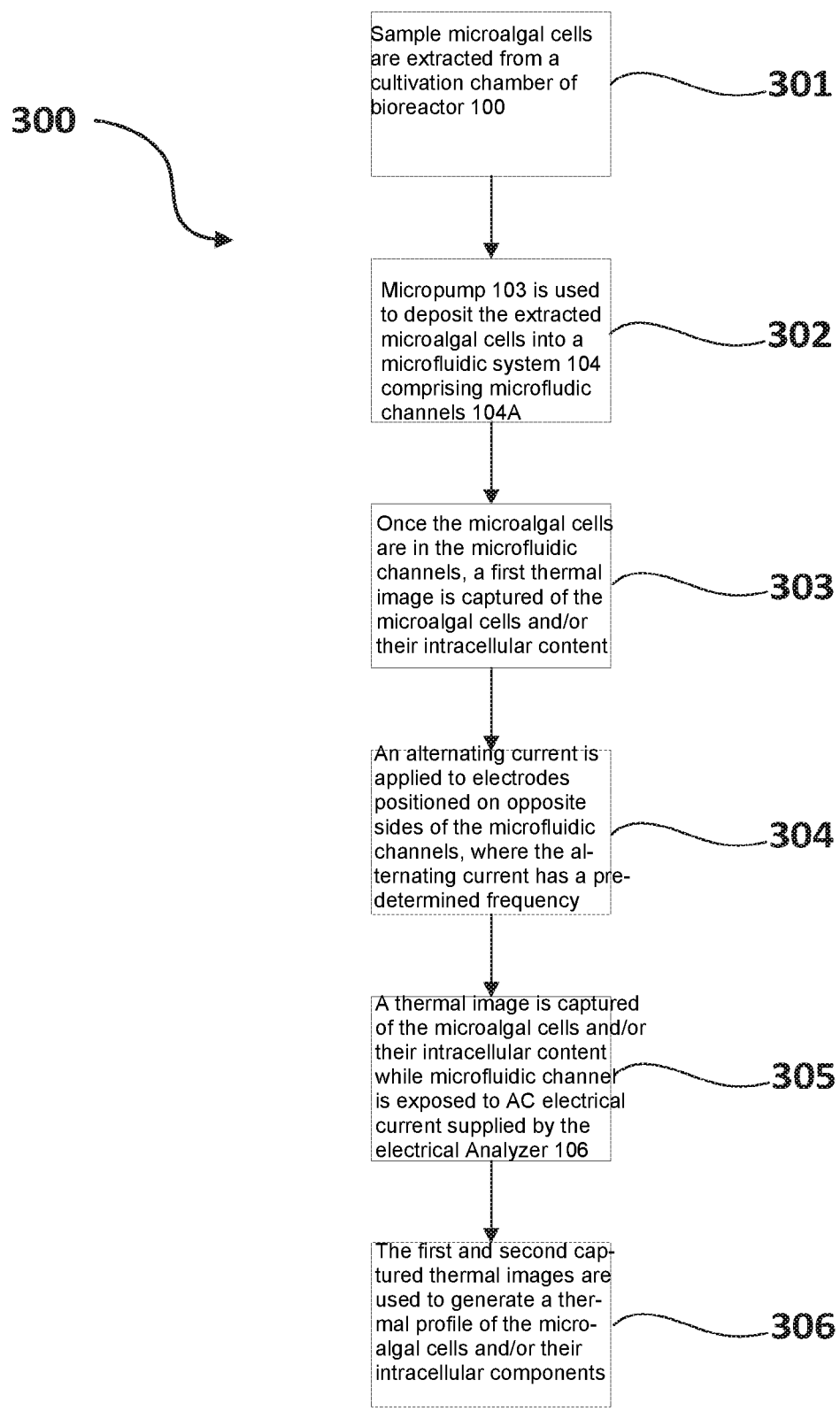
FIG. 3 shows a flow chart describing the steps of the method used to obtain real time, in-situ measurement of intracellular contents of the microalgal culture present in the cultivation chamber of the bioreactor system shown in FIG. 1.

Referring to FIG. 3, a flow chart is shown in which a method of operating system 100 is described for identification and quantification of intracellular components in a cell culture such as microalgal cells extracted from the bioreactor cultivation chamber in accordance with an exemplary embodiment of the present disclosure. In this embodiment, the system 100 is operated in accordance with a method 300 to identify and quantify the intracellular components. In step 301, sample microalgal cells are extracted from a cultivation chamber of bioreactor 100. In the embodiment described in FIG. 1, the extraction is performed using a micropump 103. In step 302, the micropump 103 is used to deposit the extracted microalgal cells into a microfluidic system 104 comprising microfluidic channels 104A. In step 303, once the microalgal cells are in the microfluidic channels, a first thermal image is captured of the microalgal cells and/or their intracellular content. The thermal image capturing is performed using thermal camera 108. In step 304, an alternating current is applied to electrodes positioned on opposite sides of the microfluidic channels, where the alternating current has a pre-determined frequency. In the embodiment described in FIG. 1, an electrical analyser 106 is used to provide the AC electrical current and to control the frequency of the alternating current. In step 305, a thermal image is captured of the microalgal cells and/or their intracellular content while the microfluidic channel is exposed to the AC electrical current supplied by the electrical Analyzer 106. In step 306, the first and second captured thermal image are used to generate a thermal profile of the microalgal cells and/or their intracellular components. The thermal profile is used to characterize at least one intracellular component such as lipids, proteins or carbohydrates based on identified heat signatures of the at least one intracellular component and also based on pre-determined values of heat signatures related to known intracellular components.

In some embodiments, the pre-determined values of heat signatures may be obtained by conducting the initial steps of: using a reference sample and first marking an intracellular component in the microalgal cell of the sample using techniques such as staining, where the stain used is configured to affect only the intracellular component of interest. Once the intracellular component is marked, the cell is subjected to an AC electrical current under different frequencies and resistivity is measured. A frequency is then determined, which causes the marked intracellular component to produce a distinguished electrical resistivity compared to other intracellular components. Distinguished in this context means having a resistivity reading that is the highest in comparison to other resistivity readings resulting from other frequencies. Thermal imaging is taken of the microalgal cell before exposing it to the alternating current and while exposing it to such current and determining the frequency that causes the intracellular component to have a distinguished resistivity compared to the other intracellular components in the cell. The thermal images are then used to determine the heat signature of the marked cellular component when subjected to the resistivity distinguishing frequency. In this context, the heat signature produced will be the hottest in comparison to heat signatures produced when the microalgal cell is exposed to AC electrical current with frequencies different from the resistivity distinguishing frequency.

The above initial steps are contemplated to be done only once for each intracellular component in order to determine the heat signature of each cellular component of interest and the relevant frequency that maximized such heat signature. It is assumed that the staining agent used will not have an effect or will have a dismal effect on the electrical and thermal properties of the cellular component such that any effect may be negligible when the heat profile is generated from the difference of the captured heat images before and during application of the AC electrical current.

In some embodiments, the above initial steps may be performed but with the addition of the preliminary step of isolating the marked cellular component from the cell to determine its heat signature in isolation of other cellular components. Known techniques of weakening the cell wall and extracting the cellular component of interest may be utilised and therefore are not described in this disclosure. In such embodiment, the step of marking the intracellular component may not be required since there will be no need to distinguish the intracellular component from other components. However, the marking of the intracellular component may be used for isolating and extracting the intracellular component of interest.

In other embodiments, other techniques known in the art may be used to optimize the intracellular component of interest such as lipids in the microalgal cell. The lipids optimized microalgal cell is then subjected to alternating current and the frequency of the current is varied until a maximum resistance is achieved. In such embodiment, the marking of the intracellular component will also not be required.

Using any of the methods described above, once the resistivity distinguishing frequency is obtained for different intracellular components of interest, such values are tabulated and stored in a memory storage that is either part of the electrical analyser or external to it. Such values may be accessed by the electrical analyser during the monitoring process of the microalgal cells in the bioreactor system described above to achieve the objective of interest. For example, for biofuel processing, it is important to optimize the lipid content of the cultivation culture before sending the culture for biofuel processing. In that case, when considering a sample microalgal cell from the cultivation chamber, the alternating current will be tuned at the pre-determined frequency that causes a distinguished resistivity for lipids in comparison to other intracellular components in the microalgal cell. Subjecting the cell to such AC electrical current will cause the lipids in that cell to produce the highest heat signature compared to the other cellular components, which will allow the lipids to be identified in the sample microalgal cell based on its heat signature that is produced using thermal images of the sample captured using a thermal camera.

Since the technique used allows for the examination of the intracellular components of individual cells, the table generated for the resistivity distinguishing frequencies will allow for the characterization of the intracellular components in each cell irrespective of the cell concentration of the solution being examined. So, the cellular concentration in the solution may not be required for the characterization of the intracellular components in the solution examined.

Once identified, the quantification of the intracellular content of interest may also be achieved. In some embodiments, quantification of intracellular contents is determined based on examination of a single cell at a time. In other embodiments, a selection of cells may be examined at once and the results obtained may be averaged for accuracy. In an exemplary embodiment, the concentration of lipids in a microalgal cell may be established by calculating the ratio between the area of the sections of the heat profile that represent lipids and the sections that have no or lower heat signatures in comparison to lipids. Such ratio will provide the quantum of lipids in the cell in comparison to the intracellular content. By configuring the bioreactor to have a uniform distribution of microalgal cells in the cultivation chamber and also by ensuring that the nutritional conditioning is uniformly dispersed, it is reasonable to assume that the identification and quantification of lipids or other intracellular components in the aliquot of microalgal cell will be representative of the entire culture in the cultivation chamber. Such ratio calculation may be performed using any techniques or tools known in the art. Also, it is to be understood that other known techniques for measuring the ratio of an identified section of a cell are to be contemplated within the teaching of the present disclosure. By comparing the calculated ratio to a pre-determined threshold, the system and method described allow for assessing whether the cell culture contained in the cultivation chamber is ready for biofuel processing.

The bioreactor system and method of operating it as described in the present disclosure allows for continuous monitoring of intracellular components of interest such as lipids, proteins and carbohydrates in microalgae culture in a bioreactor system being prepared for biofuel processing and production. The system and method also allow for the identification and quantification of intracellular components in-situ, passively, non-invasively, inexpensively and in a non-labour intensive manner. The method may be integrated directly with the cultivation chamber to conduct real-time measurements to quickly obtain accurate and continuous information that may be used as feedback to control the cultivation growth conditions. Such identification may provide highly relevant data to determine if the culture is ready for biofuel processing. If the culture is not ready for biofuel processing, the data allows for the modification of the growth condition in the microalgae culture in order to achieve the lipid concentration of interest for biofuel processing.

Interpretation of Terms

Unless the context clearly requires otherwise, throughout the description and the claims:
"comprise," "comprising," and the like are to be construed in an inclusive sense, as opposed to an exclusive or exhaustive sense; that is to say, in the sense of "including, but not limited to".
"connected," "coupled," or any variant thereof, means any connection or coupling, either direct or indirect, between two or more elements; the coupling or connection between the elements can be physical, logical, or a combination thereof.
"herein," "above," "below," and words of similar import, when used to describe this specification shall refer to this specification as a whole and not to any particular portions of this specification.
"or," in reference to a list of two or more items, covers all of the following interpretations of the word: any of the items in the list, all of the items in the list, and any combination of the items in the list.
the singular forms "a", "an" and "the" also include the meaning of any appropriate plural forms.
"subject" refers to a human or other animal. It is intended that the term encompass patients, such as vocally-impaired patients, as well as inpatients or outpatients with which the present invention is used as a diagnostic or monitoring device. It is also intended that the present invention be used with healthy subjects (i.e., humans and other animals that are not vocally-impaired, nor suffering from disease). Further, it is not intended that the term be limited to any particular type or group of humans or other animals.
"power source" and "power supply" refer to any source of electrical power in a form that is suitable for operating electronic circuits.
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", "upper", "lower" and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a circuit, module, assembly, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of device and method have been described herein for purposes of illustration. These are only examples. The technology provided herein can be applied to device and method other than the examples described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

What is claimed is:
1. A method for characterizing intracellular components of a cell culture in a cultivation chamber of a bioreactor system, the method comprising:
providing a sample culture in at least one microfluidic channel of a microfluidic system of the bioreactor, the sample culture extracted from the cell culture;
applying an alternating current to the at least one microfluidic channel, the alternating current configured to have a resistivity distinguishing frequency for a component of interest from the intracellular components;
obtaining a first thermal image of the sample culture before applying the alternating current to the at least one microfluidic channel and a second thermal image of the sample culture while applying the alternating current to the at least one microfluidic channel;
generating a heat profile of the sample culture from the first thermal image and the second thermal image, the heat profile distinguishing the component of interest from the rest of the intracellular components in the sample culture;
determining the amount of the component of interest in the sample culture based on the heat profile generated; and
determining an amount of the component of interest in the cell culture based on the amount of the component of interest determined in the sample culture.

2. The method according to claim 1, wherein the heat profile is generated by subtracting the first thermal image from the second thermal image of the sample culture.

3. The method according to claim 1, wherein the resistivity distinguishing frequency for the component of interest is obtained by performing an initial step of:
providing a reference culture sample containing at least the component of interest, wherein the reference culture sample is deposited into the at least one microfluidic channel;
marking the component of interest in the reference culture sample by a marker, the marker configured to substantially not affect the resistivity of the component of interest, the rest of the intracellular components or any cultivation medium and to only identify the component of interest from the rest of the intracellular components and the cultivation medium in the reference culture sample;

applying alternating currents to the at least one microfluidic channel, the alternating currents sweeping over a frequency range;

measuring the resistivity of the marked component of interest for each frequency of the frequency range; and identifying the resistivity distinguishing frequency for the component of interest in the reference culture sample, wherein the resistivity of the marked component of interest represents the highest measured resistivity.

4. The method according to claim 3, wherein identifying the resistivity distinguishing frequency for the component of interest in the reference culture sample at the highest measured frequency is performed by:

obtaining thermal images of the reference culture sample before and during applying the alternating currents;

generating a heat profile of the reference culture sample based on the thermal images; and determining a heat signature of the marked component of interest based on the heat profile, the heat signature corresponding to the highest identified temperature in the heat profile and corresponding to the resistivity of the marked component of interest when the alternating current with the resistivity distinguishing frequency is applied to the reference culture sample.

5. The method according to claim 4, the method further comprises generating a reference library of the resistivity distinguishing frequency and the corresponding heat signature for each component of the intracellular components.

6. The method according to claim 5, wherein characterizing the intracellular component of the sample culture comprises:

selecting from the reference library the resistivity distinguishing frequency for the component of interest; and identifying if the component of interest is present in the sample culture based on comparing heat signatures values from the generated heat profile for the sample culture with the heat signature value from the reference library.

7. The method according to claim 6, wherein once the component of interest is identified, the step of characterizing the intracellular component of the sample culture further comprises determining the amount of the component of interest by determining based on the heat signatures in the heat profile a ratio of the identified component of interest to the rest of the intracellular components and the cultivation medium.

8. The method according to claim 1, wherein the cell culture comprises microalgae cells culture, the component of interest is lipids and the intracellular components comprise lipids, carbohydrates and proteins and wherein the method is used for optimizing the lipids' content in the microalgae cells culture for biofuel processing.

9. The method according to claim 8, wherein optimizing the lipids' content in the microalgae cells culture is performed by continuously monitoring in-situ the amount of lipids in samples extracted from the microalgae cells culture and determining that the microalgae cells culture is ready for biofuel processing when a pre-determined threshold of lipid content is achieved in the microalgae cells culture.

10. The method according to claim 9, wherein the method comprises returning the samples extracted from the microalgae cells culture back to the cultivation chamber after characterizing the intracellular components in the samples.

11. A system for characterizing intracellular components of a cell culture in a bioreactor, the system comprising:

a cultivation chamber for housing the cell culture;

a microfluidic system in fluid communication with the cultivation chamber, the microfluidic system having at least one microfluidic channel configured for holding a sample culture from the cell culture;

an electrical analyzer in electrical communication with the microfluidic system, the electrical analyzer configured for applying to the at least one microfluidic channel an alternating current with a resistivity distinguishing frequency for a component of interest from the intracellular components;

a thermal camera configured for obtaining a first thermal image of the sample culture before exposing the at least one microfluidic channel to the alternating current and a second thermal image of the sample culture while exposing the at least one microfluidic channel to the alternating current;

a processor configured for generating a heat profile of the sample culture from the first thermal image and the second thermal image, the heat profile distinguishing the component of interest from remaining components of the intracellular components of the sample culture, the processor also configured to identify and quantify the component of interest in the sample culture and the cell culture based on the generated heat profile.

12. The system according to claim 11, the system further comprising a micropump coupled to the microfluidic system and the cultivation chamber, the micropump configured for extracting the sample culture from the cultivation chamber and for depositing the extracted sample culture to the at least one microfluidic channel.

13. The system according to claim 11, wherein the at least one microfluidic channel comprises more than one microfluidic channel.

14. The system according to claim 13, wherein the more than one microfluidic channels are formed in the microfluidic system to be parallel to one another and wherein each of the more than one microfluidic channels is electrically coupled to the electrical analyzer.

15. The system according to claim 14, wherein the electrical analyzer is configured to supply one of same or different voltage and alternating current for each of the more than one microfluidic channels.

16. The system according to claim 11, wherein the microfluidic system has an inlet in fluid communication with the cultivation chamber, the intel configured for receiving the sample culture from the cultivation chamber and for allowing cells in the sample culture to flow into the microfluidic system and be positioned in the at least one microfluidic channel such that the cells are examined either one at a time or as a group.

17. The system according to claim 11, wherein the microfluidic system has an outlet for discharging the sample culture after characterizing its intracellular contents and wherein the outlet is in fluid communication with the cultivation chamber so that when the sample culture is discharged from the microfluidic system, the sample culture is returned to the cultivation chamber.

18. The system according to claim 11, wherein the system further comprises sensors positioned near the at least one microfluidic channel, the sensors configured for detecting the presence of the sample culture in the at least one microfluidic channel and for signaling the thermal camera to start or stop taking images of the sample culture.

19. The system according to claim 11, the system further comprising a memory storage device for storing a predetermined resistivity distinguishing frequency and heat signature corresponding to each component of the intracellular components, wherein the resistivity distinguishing frequencies correspond to a frequency for which when the component of interest is exposed to the alternating current, the resistivity of the component of interest is highest and wherein the heat signatures correspond a heat signature for which when the component of interest is exposed to the alternating current, the temperature of the component of interest is highest, and wherein the memory storage device is accessible by the processor to retrieve the resistivity distinguishing frequency for the component of interest and the heat signature of the component of interest to allow for the identification and quantification of the component of interest in the sample culture.

20. The system according to claim 11, wherein the system is configured such that the cell culture is uniformly distributed and nutritional conditioning is uniformly dispersed in the cultivation chamber.

* * * * *